United States Patent
Hayashida et al.

(10) Patent No.: US 10,251,694 B2
(45) Date of Patent: Apr. 9, 2019

(54) OPERATION METHOD OF ELECTRIC POWER SOURCE DEVICE, ELECTRIC POWER SOURCE DEVICE, AND HIGH-FREQUENCY TREATMENT SYSTEM

(71) Applicant: OLYMPUS CORPORATION, Hachioji-shi, Tokyo (JP)

(72) Inventors: Tsuyoshi Hayashida, Hachioji (JP); Danilo Legaspi, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/645,738

(22) Filed: Jul. 10, 2017

(65) Prior Publication Data

US 2017/0303988 A1    Oct. 26, 2017

Related U.S. Application Data

(63) Continuation of application No. PCT/JP2016/064617, filed on May 17, 2016.

(30) Foreign Application Priority Data

Jul. 30, 2015 (JP) .................................. 2015-150468

(51) Int. Cl.
*A61B 18/14* (2006.01)
*A61B 18/12* (2006.01)
(Continued)

(52) U.S. Cl.
CPC .. *A61B 18/1206* (2013.01); *A61B 17/320068* (2013.01); *A61B 18/14* (2013.01);
(Continued)

(58) Field of Classification Search
CPC ................ A61B 218/00755; A61B 218/00767
See application file for complete search history.

(56) References Cited

U.S. PATENT DOCUMENTS 5,540,684 A * 7/1996 Hassler, Jr. ........ A61B 18/1206
606/38
2003/0158551 A1    8/2003 Paton et al.
(Continued)

FOREIGN PATENT DOCUMENTS

JP    H08-98845 A    4/1996
JP    2002-502660 A    1/2002
(Continued)

OTHER PUBLICATIONS

Jul. 18, 2017 Office Action issued in Japanese Application No. 2017-503962.
(Continued)

*Primary Examiner* — Ronald Hupczey, Jr.
*Assistant Examiner* — Bo Ouyang
(74) *Attorney, Agent, or Firm* — Oliff PLC

(57) ABSTRACT

An operation method of an electric power source device for operating a high-frequency treatment instrument configured to perform a high-frequency treatment on a biological tissue includes causing a high-frequency electric power source circuit to output electric power; specifying an initial state of the biological tissue; acquiring a value relating to an impedance of the biological tissue; determining an additional impedance value based on the initial state; setting a stop impedance value which is the sum of the additional impedance value and a change-over impedance value; and causing the high-frequency electric power source circuit to stop the output, if the value relating to the impedance reaches the stop impedance value after the value relating to the impedance reached the change-over impedance value.

13 Claims, 9 Drawing Sheets

(51) Int. Cl.
*A61B 17/32* (2006.01)
*A61B 18/00* (2006.01)

(52) U.S. Cl.
CPC ...... *A61B 18/1442* (2013.01); *A61B 18/1445* (2013.01); *A61B 2018/0063* (2013.01); *A61B 2018/00678* (2013.01); *A61B 2018/00755* (2013.01); *A61B 2018/00767* (2013.01); *A61B 2018/00875* (2013.01)

(56) References Cited

U.S. PATENT DOCUMENTS

| | | | |
|---|---|---|---|
| 2011/0144635 A1* | 6/2011 | Harper | A61B 18/1206 606/34 |
| 2011/0319882 A1 | 12/2011 | Kennedy et al. | |
| 2012/0283731 A1* | 11/2012 | Unger | A61B 18/1206 606/49 |
| 2013/0066238 A1 | 3/2013 | Irisawa et al. | |

FOREIGN PATENT DOCUMENTS

| | | | |
|---|---|---|---|
| JP | 2005-517498 A | 6/2005 |
| JP | 2007-319684 A | 12/2007 |
| JP | 2011-125714 A | 6/2011 |
| JP | 2012-196458 A | 10/2012 |

OTHER PUBLICATIONS

Jul. 12, 2016 International Search Report issued in International Patent Application No. PCT/JP2016/064617.
Jan. 30, 2018 International Preliminary Report on Patentability issued in International Patent Application No. PCT/JP2016/064615.
Jan. 30, 2018 International Preliminary Report on Patentability issued in International Patent Application No. PCT/JP2016/064616.
Jan. 30, 2018 International Preliminary Report on Patentability issued in International Patent Application No. PCT/JP2016/064617.
May 24, 2018 Office Action issued in U.S. Appl. No. 15/784,261.
Mar. 21, 2017 Office Action issued in Japanese Patent Application No. 2017-503962.
Jul. 12, 2016 International Search Report issued in Patent Application No. PCT/JP2016/064615.
Jul. 12, 2016 International Search Report issued in Patent Application No. PCT/JP2016/064616.
Mar. 21, 2017 Office Action issued in Patent Application No. PCT 2017-503962.
Sep. 25, 2018 Office Action issued in U.S. Appl. No. 15/784,261.
Nov. 15, 2018 Search Report issued in European Patent Application No. 16830128.1.
Jan. 7, 2019 Extended European Search Report issued in European Patent Application No. 16830130.7.

\* cited by examiner

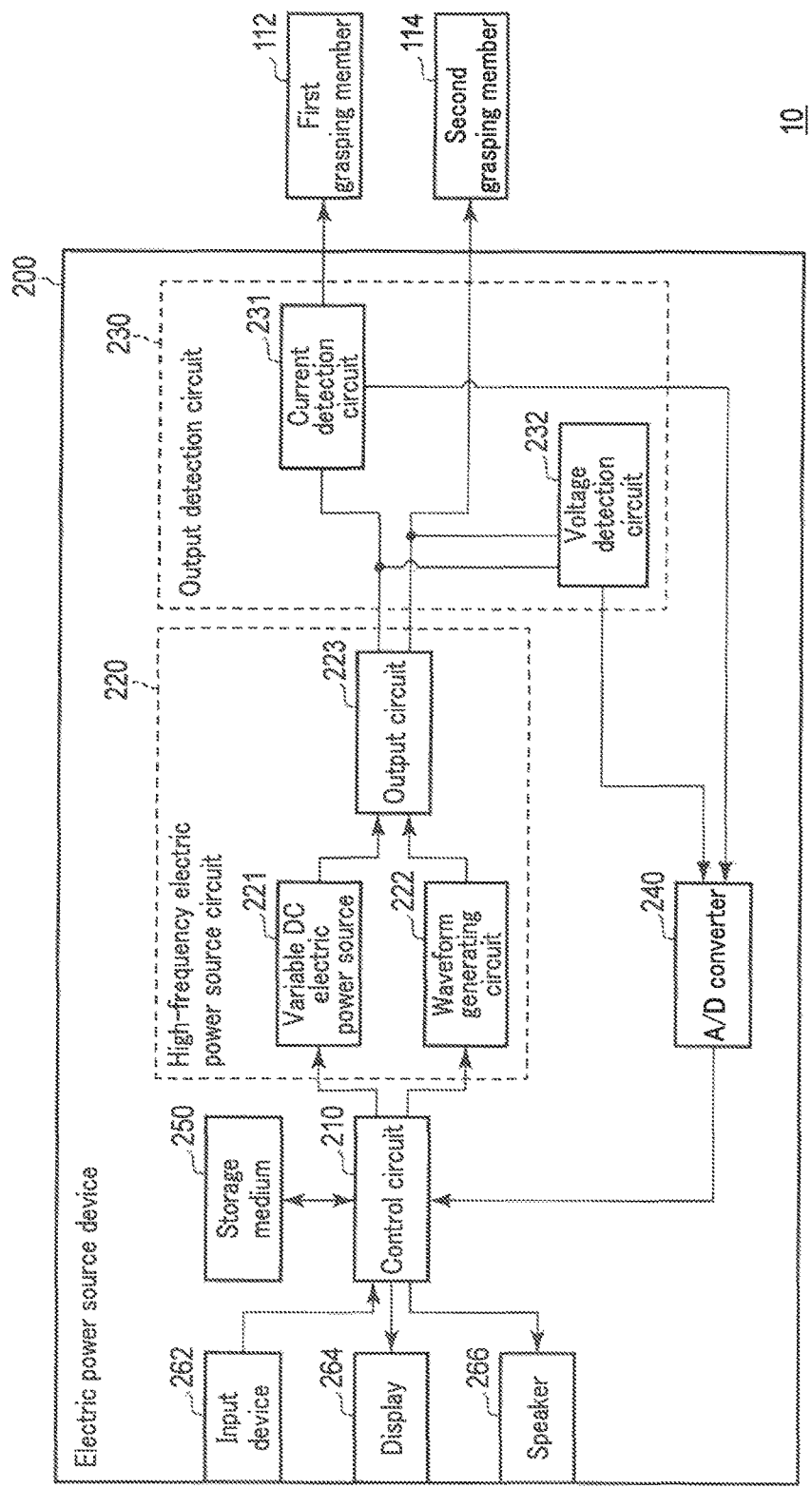
F I G. 2

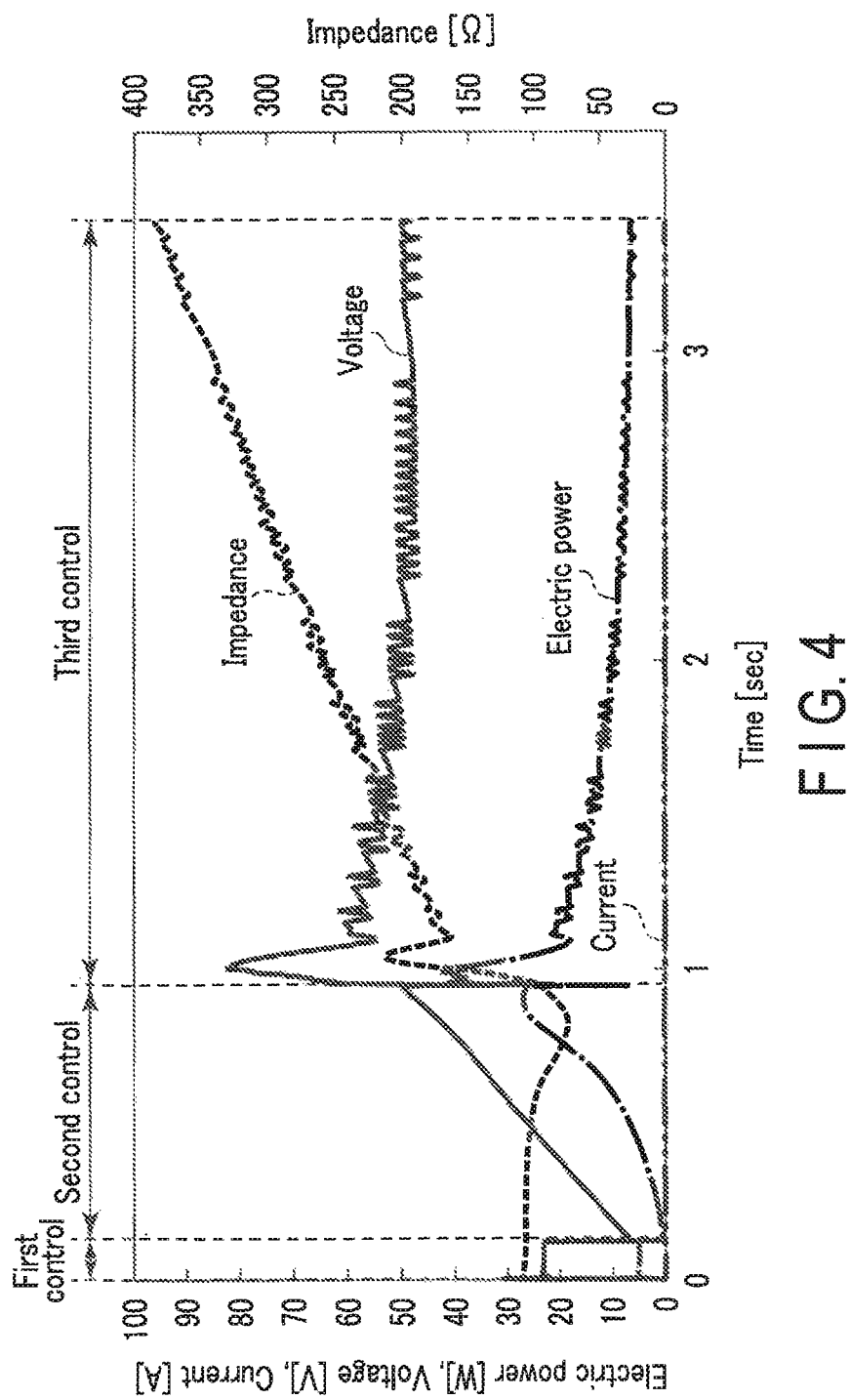
F I G. 4

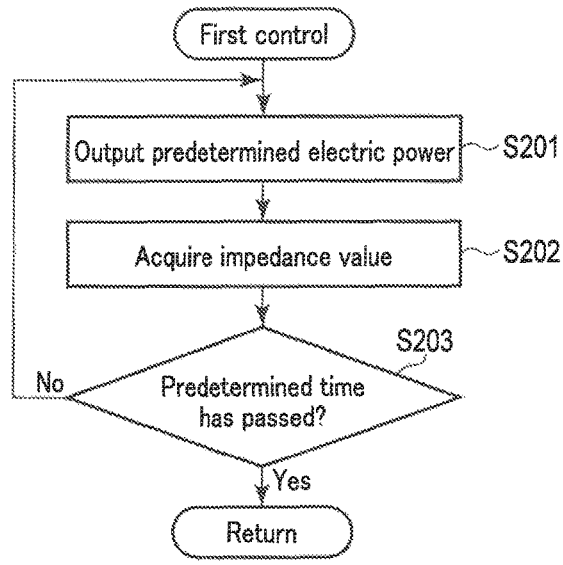
F I G. 5
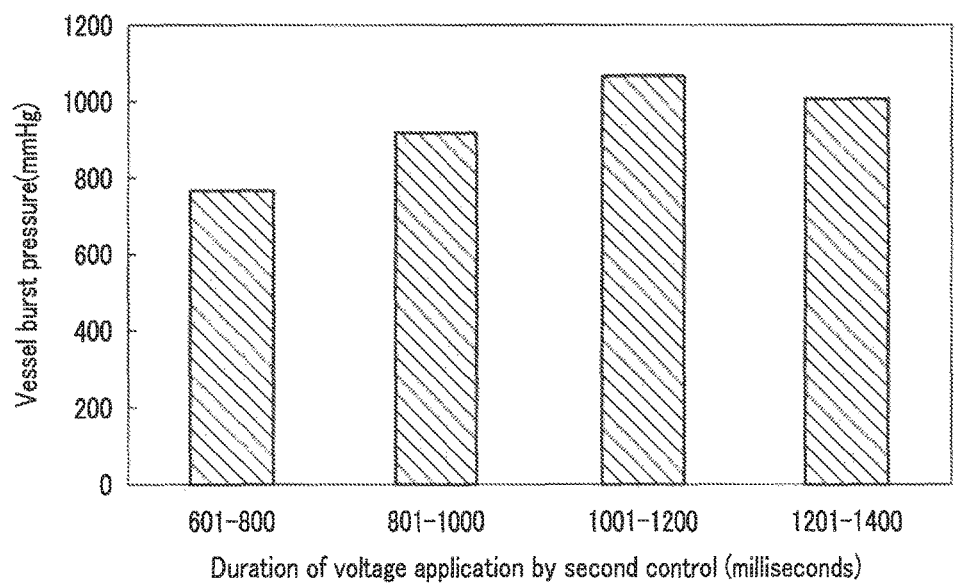
F I G. 6

| Initial resistance value R0 | a | b | c | d |
|---|---|---|---|---|
| Additional resistance value Radd | 400 | 350 | 300 | 250 |

| Initial resistance value R0 / Duration Dt | a | b | c | d |
|---|---|---|---|---|
| 0-0.5 seconds | 250 | 250 | 250 | 200 |
| 0.5-1.0 seconds | 350 | 350 | 300 | 250 |
| 1.0 seconds or more | 400 | 400 | 350 | 300 |

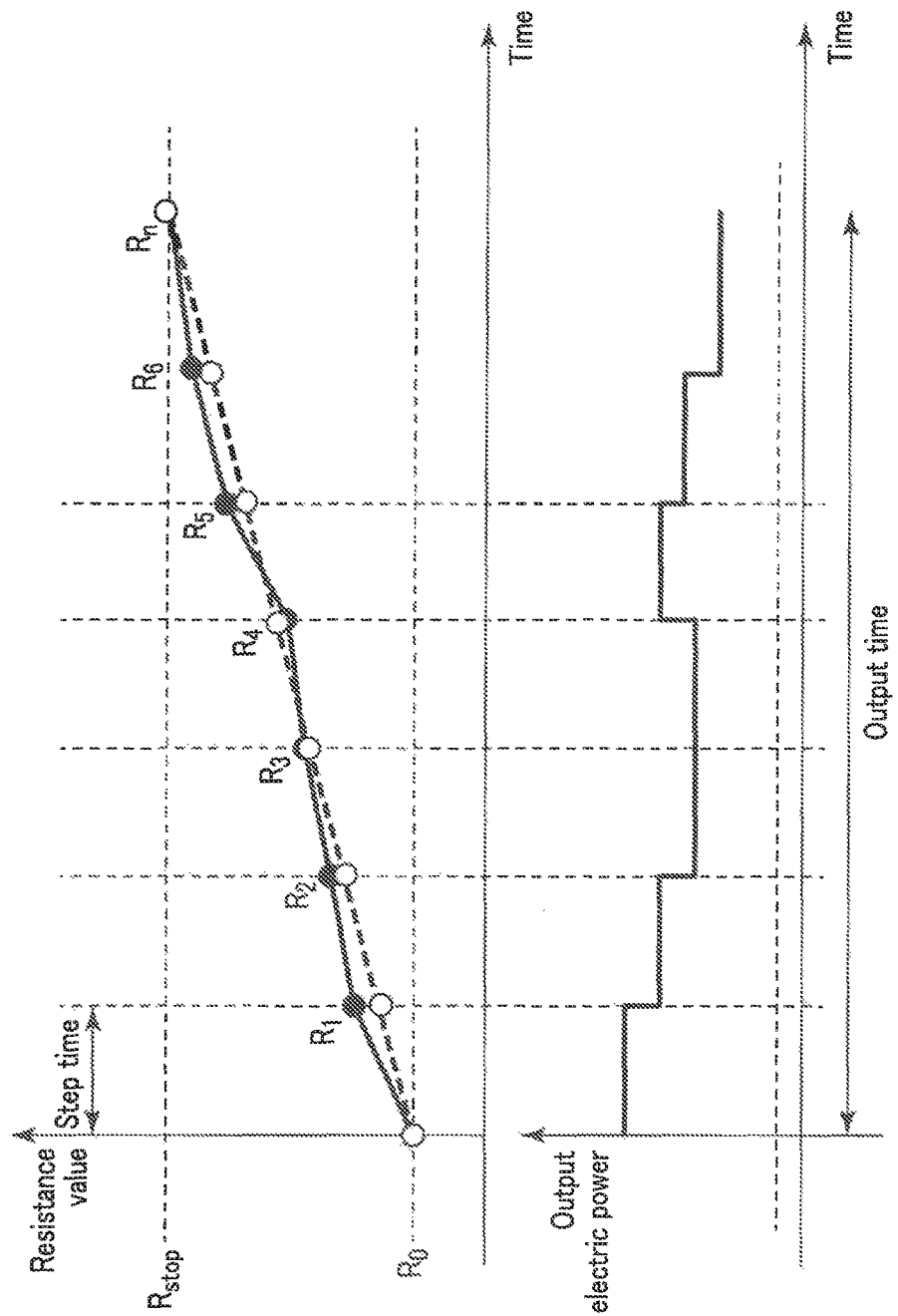
F I G. 11

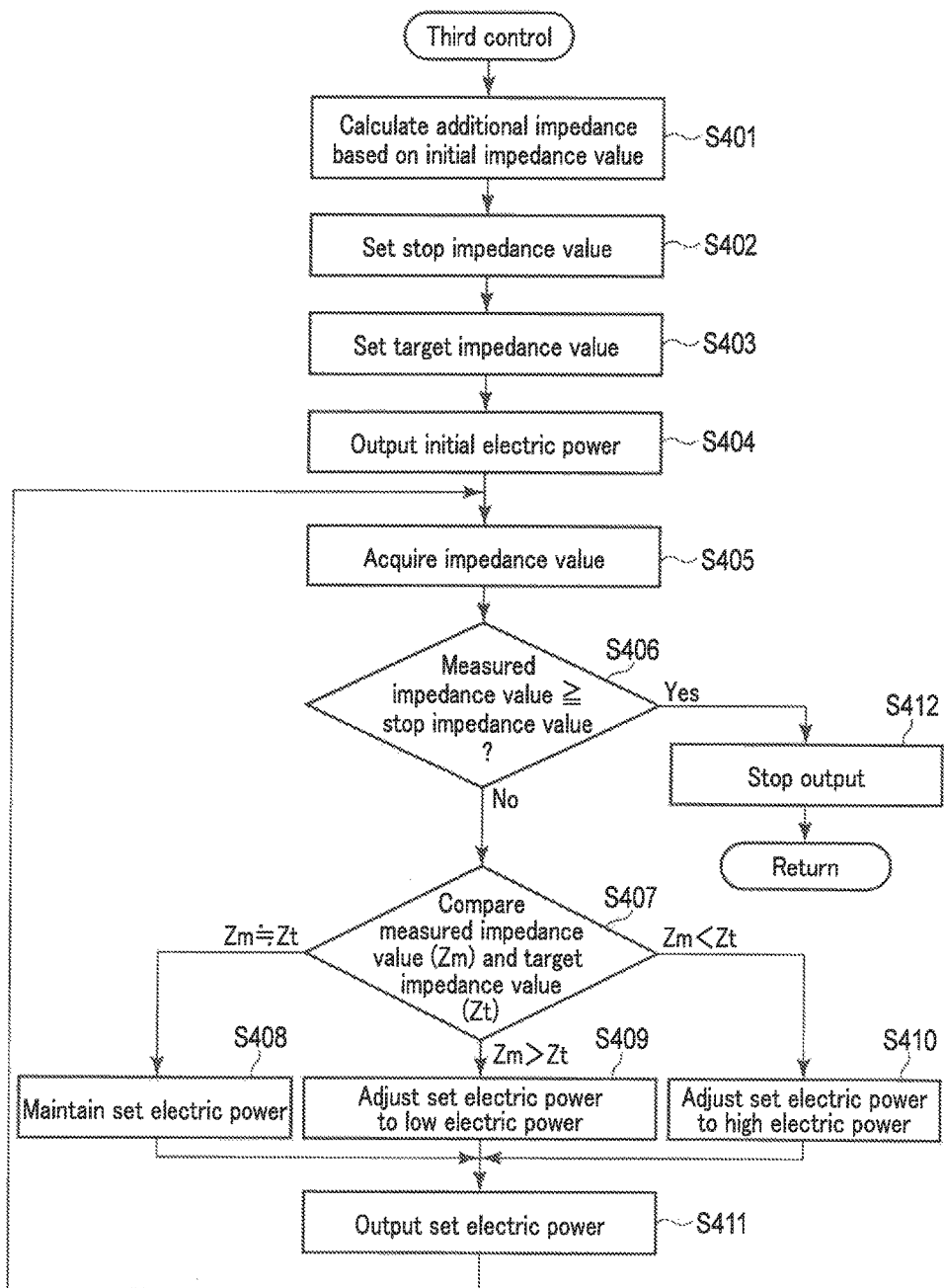
F I G. 12

OPERATION METHOD OF ELECTRIC POWER SOURCE DEVICE, ELECTRIC POWER SOURCE DEVICE, AND HIGH-FREQUENCY TREATMENT SYSTEM

CROSS-REFERENCE TO RELATED APPLICATIONS

This application is a Continuation Application of PCT Application No. PCT/JP2016/064617, filed May 17, 2016 and based upon and claiming the benefit of priority from prior Japanese Patent Application No. 2015-150468, filed Jul. 30, 2015, the entire contents of all of which are incorporated herein by reference.

BACKGROUND OF THE INVENTION

1. Field of the Invention

The present invention relates to an operation method of an electric power source device for operating a high-frequency treatment instrument, an electric power source device, and a high-frequency treatment system.

2. Description of the Related Art

In general, there is known a high-frequency treatment system which performs a treatment by grasping a biological tissue, which is a treatment target, by a pair of grasping members, and by supplying high-frequency electric power to the biological tissue. In this system, the biological tissue grasped by the grasping members is heated by a high-frequency current flowing through the biological tissue. This high-frequency treatment system is used for, for example, sealing a blood vessel. In the high-frequency treatment system, in order to improve the precision and efficiency of the treatment, it is required to appropriately adjust an output voltage and an output current.

For example, Jpn. Pat. Appln. KOKAI Publication No. H8-98845 discloses a technique relating to controlling an output by paying attention to an impedance value of a biological tissue. Specifically, in this technique, a maximum value and a minimum value of the impedance value measured at an initial stage of a treatment are specified. The impedance value, which is measured during the treatment, rises after taking a minimum value. In the process of rising, the output is stopped when the impedance value reaches a predetermined value between the specified maximum value and minimum value. It is considered preferable that this value between the maximum value and minimum value is, for example, a mean value between the maximum value and minimum value.

In addition, for example, Jpn. Pat. Appln. KOKAI Publication No. 2012-196458 discloses a technique relating to setting a target value with respect to the transition of the impedance value during the treatment, and controlling the output such that this target value and the measured actual impedance value become equal.

In the high-frequency treatment system, since the adjustment of the output voltage and output current affects the precision and efficiency of the treatment, it is required that the output voltage and output current be adjusted more appropriately. In addition, it is known that the optimal output voltage and output current vary in accordance with a treatment target. Accordingly, it is required that the output voltage and output current be adjusted in accordance with a treatment target.

BRIEF SUMMARY OF THE INVENTION

According to an aspect of the invention, an operation method of an electric power source device for operating a high-frequency treatment instrument configured to perform a high-frequency treatment on a biological tissue includes causing, by a control circuit, a high-frequency electric power source circuit to output electric power; specifying, by the control circuit, an initial state of the biological tissue in a first period from a start of the output; acquiring, by the control circuit, a value relating to an impedance of the biological tissue, after specifying the initial state of the biological tissue; determining an additional impedance value, based on the initial state; setting, by the control circuit, a stop impedance value which is the sum of the additional impedance value and a change-over impedance value, where the change-over impedance value is a value relating to the impedance indicative of a predetermined state; and causing, by the control circuit, the high-frequency electric power source circuit to stop the output, if the value relating to the impedance reaches the stop impedance value after the value relating to the impedance reached the change-over impedance value.

According to an aspect of the invention, an electric power source device for operating a high-frequency treatment instrument is configured to perform a high-frequency treatment on a biological tissue. The device includes a high-frequency electric power source circuit configured to output electric power; an output detection circuit configured to detect the output; and a control circuit configured to acquire information relating to the output from the output detection circuit, and configured to control an operation of the high-frequency electric power source circuit. The control circuit is configured to execute causing the high-frequency electric power source circuit to output the electric power; specifying an initial state of the biological tissue in a first period from a start of the output; acquiring a value relating to an impedance of the biological tissue, after specifying the initial state of the biological tissue; determining an additional impedance value, based on the initial state; setting a stop impedance value which is the sum of the additional impedance value and a change-over impedance value, where the change-over impedance value is a value relating to the impedance indicative of a predetermined state; and causing the high-frequency electric power source circuit to stop the output, if the value relating to the impedance reaches the stop impedance value after the value relating to the impedance reached the change-over impedance value.

According to an aspect of the invention, a high-frequency treatment system includes the above-mentioned electric power source device; and the high-frequency treatment instrument.

Advantages of the invention will be set forth in the description which follows, and in part will be obvious from the description, or may be learned by practice of the invention. The advantages of the invention may be realized and obtained by means of the instrumentalities and combinations particularly pointed out hereinafter.

BRIEF DESCRIPTION OF THE SEVERAL VIEWS OF THE DRAWINGS

The accompanying drawings, which are incorporated in and constitute a part of the specification, illustrate embodiments of the invention, and together with the general description given above and the detailed description of the embodiments given below, serve to explain the principles of the invention.

FIG. 2 is a block diagram which schematically illustrates a configuration example of the high-frequency treatment system according to the embodiment.

FIG. 4 shows an example of variations of an electric power, a voltage, a current and an impedance relative to time in the high-frequency treatment system according to the embodiment.

FIG. 5 is a flowchart illustrating an example of first control of the high-frequency treatment system according to the embodiment.

FIG. 6 shows an example of the relationship between duration of application of a voltage to a biological tissue in second control and a vessel burst pressure of a blood vessel which is sealed by the treatment.

FIG. 11 shows an example of a graph of an output electric power and a resistance value versus time in the high-frequency treatment system according to the embodiment.

FIG. 12 is a flowchart illustrating an example of third control of the high-frequency treatment system according to the embodiment.

DETAILED DESCRIPTION OF THE INVENTION

Figure 1:
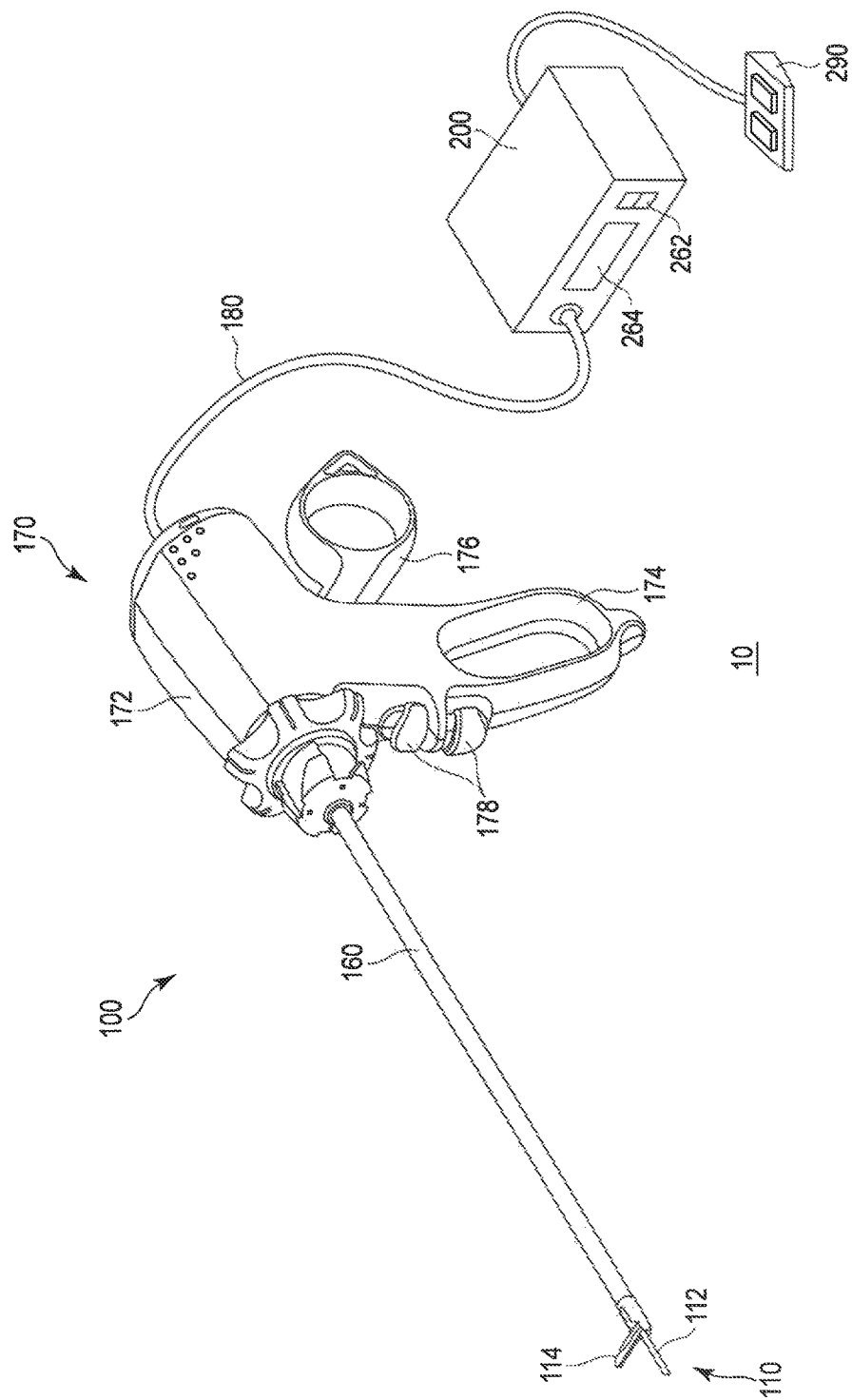
FIG. 1 is a view which schematically illustrates an example of the external appearance of a high-frequency treatment system according to an embodiment.

An embodiment of the present invention will be described hereinafter with reference to the accompanying drawings. FIG. 1 is a schematic view of a high-frequency treatment system 10 according to the present embodiment. As illustrated in this Figure, the high-frequency treatment system 10 includes a high-frequency treatment instrument 100 which functions as a high-frequency treatment instrument, an electric power source device 200 which supplies electric power to the treatment instrument, and a footswitch 290.

The high-frequency treatment instrument 100 includes a treatment portion 110, a shaft 160, and an operation portion 170. For the purpose of descriptions below, the treatment portion 110 side is referred to as a distal side, and the operation portion 170 side is referred to as a proximal side. The high-frequency treatment system 10 is configured to grasp a biological tissue, such as a blood vessel, which is a treatment target, by the treatment portion 110. The high-frequency treatment system 10 applies a high-frequency voltage to the grasped biological tissue, thereby sealing this biological tissue.

The treatment portion 110, which is provided at a distal end of the shaft 160, is provided with a first grasping member 112 and a second grasping member 114, which are a pair of grasping members. Those parts of the first grasping member 112 and second grasping member 114, which come in contact with the biological tissue, function as electrodes, respectively. Specifically, the first grasping member 112 and second grasping member 114 function as bipolar electrodes.

The operation portion 170 is provided an operation portion main body 172, a stationary handle 174, a movable handle 176, and an output switch 178. The stationary handle 174 is fixed to the operation portion main body 172, and the movable handle 176 is displaced relative to the operation portion main body 172. The movable handle 176 is connected to a wire or a rod, which is inserted through the shaft 160. This wire or rod is connected to the second grasping member 114. The movement of the movable handle 176 is transmitted to the second grasping member 114. The second grasping member 114 is displaced relative to the first grasping member 112 in accordance with the movement of the movable handle 176. As a result, the first grasping member 112 and second grasping member 114 open or close relative to each other.

The output switch 178 includes, for example, two buttons. These buttons are buttons which are pressed when high-frequency electric power is made to act on the biological tissue, which is the treatment target, by the treatment portion 110. The electric power source device 200, which detects the pressing of the button, applies a high-frequency voltage between the first grasping member 112 and second grasping member 114. As a result, the biological tissue, which is grasped by the treatment portion 110, is sealed. The high-frequency treatment instrument 100 is configured, for example, such that the output level varies depending on which of the two buttons is pressed. The footswitch 290 is also provided with, for example, two switches. The two respective switches f the footswitch 290 have the same functions as the respective buttons of the output switch 178. The high-frequency treatment system 10 may be provided with both the output switch 178 and the footswitch 290, or may be provided with one of them. Hereinafter, a description will be given on the assumption that the output switch 178 is mainly operated, but the footswitch 290 may be operated.

One end of a cable 180 is connected to the proximal side of the operation portion 170. The other end of the cable 180 is connected to the electric power source device 200. The electric power source device 200 controls the operation of the high-frequency treatment instrument 100, and supplies electric power to the high-frequency treatment instrument 100.

FIG. 2 is a block diagram which schematically illustrates a configuration example of the electric power source device 200. The electric power source device 200 includes a control circuit 210, a high-frequency electric power source circuit 220, an output detection circuit 230, an A/D converter 240, a storage medium 250, an input device 262, a display 264, and a speaker 266.

The control circuit 210 includes an integrated circuit or the like, such as a central processing unit (CPU), an application specific integrated circuit (ASIC), or a field programmable gate array (FPGA). The control circuit 210 may be composed of a single integrated circuit or the like, or may be composed of a combination of a plurality of integrated circuits or the like. The operation of the control circuit 210 is executed, for example, in accordance with a program stored in the control circuit 210 or in the storage medium 250. The control circuit 210 acquires information from each component of the electric power source device 200, and controls the operation of each component.

The high-frequency electric power source circuit 220 outputs high-frequency electric power which is supplied to the high-frequency treatment instrument 100. The high-frequency electric power source circuit 220 includes a variable DC electric power source 221, a waveform generating circuit 222, and an output circuit 223. The variable DC electric power source 221 outputs DC electric power under the control of the control circuit 210. The output of the variable DC electric power source 221 is transmitted to the output circuit 223. The waveform generating circuit 222 generates an AC waveform under the control of the control circuit 210, and outputs the generated AC waveform. The output of the waveform generating circuit 222 is transmitted to the output circuit 223. The output circuit 223 superimposes the output of the variable DC electric power source 221 and the output of the waveform generating circuit 222, and outputs AC electric power. This AC electric power is supplied, via the output detection circuit 230, to the first grasping member 112 and second grasping member 114 of the high-frequency treatment instrument 100.

The output detection circuit 230 includes a current detection circuit 231 and a voltage detection circuit 232. The current detection circuit 231 is inserted in a circuit from the high-frequency electric power source circuit 220 to the high-frequency treatment instrument 100, and outputs an analog signal which represents a current value that is output from the high-frequency electric power source circuit 220. The voltage detection circuit 232 outputs an analog signal which represents an output voltage of the high-frequency electric power source circuit 220.

The output signal of the current detection circuit 231 and the output signal of the voltage detection circuit 232 are input to the A/D converter 240. The A/D converter 240 converts the input analog signals to a digital signal, and sends the digital signal to the control circuit 210. In this manner, the control circuit 210 acquires information of the output voltage and output current of the high-frequency electric power source circuit 220. In addition, based on the output voltage and output current, the control circuit 210 calculates a value relating to an impedance of a circuit including the first grasping ember 112, the biological tissue that is the treatment target, and the second grasping member 114. Specifically, the control circuit 210 acquires a value relating to the impedance of the biological tissue.

The storage medium 250 stores programs which are used in the control circuit 210, and various parameters, tables, etc. which are used in calculations executed in the control circuit 210.

The input device 262 includes an input device such as a button, a slider, a dial, a keyboard, or a touch panel. The control circuit 210 acquires an input to the input device 262 by the user. The display 264 includes a display device such as a liquid crystal display or an LED lamp. The display 264 presents information relating to the high-frequency treatment system 10 to the user, under the control of the control circuit 210. The speaker 266 issues, for example, an input sound, an output sound, an alarm sound, etc., under the control of the control circuit 210.

The operation of the high-frequency treatment system 10 according to the present embodiment will be described. The user operates the input device 2 of the electric power source device 200, and sets a desired output level for the high-frequency treatment instrument 100. The output level is set, for example, for each of the plural output switches 178.

The treatment portion 110 and shaft 160 are inserted, for example, into peritoneal cavity through an abdominal wall. The user opens or closes the treatment portion 110 by operating the movable handle 176. In this manner, the first grasping member 112 and second grasping member 114 grasp the biological tissue that is the treatment target. When the biological tissue is grasped by the treatment portion 110, the user operates the output switch 178. The control circuit 210 of the electric power source device 200, which detected the pressing of the button of the output switch 178, outputs an instruction, which relates to driving, to the high-frequency electric power source circuit 220.

The high-frequency electric power source circuit 220 applies, under the control of the control circuit 210, a high-frequency voltage to the first grasping member 112 and second grasping member 114 of the treatment portion 110, and causes a high-frequency current to flow through the biological tissue that is the treatment target. If the high-frequency current flows, the biological tissue becomes an electrical resistance. Thus, heat is generated in the biological tissue, and the temperature of the biological tissue rises. As a result, the protein of the biological tissue is denatured, and the biological tissue is sealed. By the above, the treatment of the biological tissue is completed.

Figure 3:
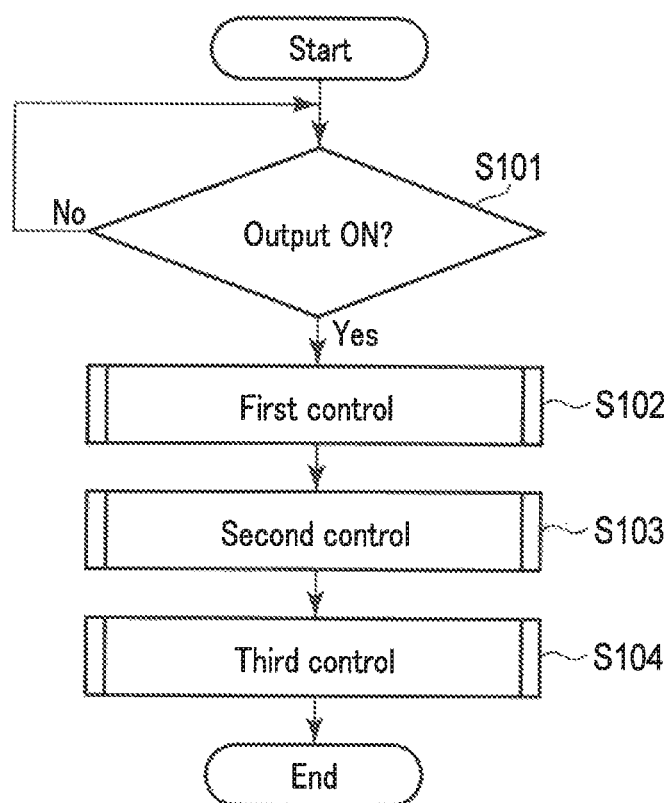
FIG. 3 is a flowchart illustrating an example of the operation of the high-frequency treatment system according to the embodiment.

The output operation of the electric power source device 200 will be described in detail. The outline of the operation of the electric power source device 200 according to the present embodiment will be described with reference to a flowchart of FIG. 3. In step S101, the control circuit 210 determines whether the output switch 178 is turned on. If the output switch 178 is not turned on, the process returns to step S101. In other words, the control circuit 210 stands by until the output switch 178 is turned on. When the output switch 178 is turned on, the process advances to step S102. In step S102, the control circuit 210 executes first control. Then, in step S103, the control circuit 210 executes second control. Subsequently, in step S104, the control circuit 210 executes third control. The first control, second control and third control will be described later in detail. By the above, the output control is terminated. In this manner, in the present embodiment, three-stage controls are executed.

Referring to FIG. 4, a description is given of an example of an output of the high-frequency treatment system 10 according to the embodiment, and an impedance relating to the biological tissue, which is calculated at the time of the output. In FIG. 4, the horizontal axis indicates time, which is set such that an output start time is 0. The left vertical axis indicates an output electric power, an output voltage, and an output current. The right vertical axis indicates an impedance. In FIG. 4, a solid line indicates a variation of the output voltage, a dashed line indicates a variation of the impedance, a dashed-dotted line indicates a variation of the output electric power, and a dashed double-dotted line indicates a variation of the output current.

As described above, the control of the output of the high-frequency treatment system 10 according to the present embodiment is divided into three stages (three phases). Accordingly, the period, during which electric power is supplied to the biological tissue, includes a first period in which the first control of a short period immediately after the output start is executed, a subsequent second period in which the second control of about one second is executed, and a subsequent third period in which the third control of about two seconds is executed. The output by the first control is referred to as a first output, the output by the second control is referred to as a second output, and the output by the third control is referred to as a third output. In addition, since the output by the second control is executed prior to the output by the third control, the period by the second control is referred to as a former period, and the period by the third control is referred to as a latter period.

In the first control, high-frequency electric power having a predetermined electric power value is supplied to the biological tissue during a predetermined period. This first period is, for example, about 100 milliseconds. During the first period, the value relating to the impedance is acquired. In accordance with the size, kind, etc. of the biological tissue that is the treatment target, or the state of the biological tissue, the value relating to the impedance, which is acquired at that time, will vary. Thus, in the present embodiment, based on the value relating to the impedance which is acquired in the first period in which the first control is executed, the state of the biological tissue that is the treatment target is ascertained, and control parameters, which are used in the subsequent control, are determined. Specifically, the control parameters, which correspond to characteristics of the biological tissue that is the treatment target, are set. In addition, in the first control, an overshoot of the output is suppressed by a predetermined electric power, which is not so large, being supplied to the biological tissue.

In the second control, a voltage which increases linearly is applied to the biological tissue. The temperature of the biological tissue rises in the second period in which the second control is executed. The second control is executed until it is detected that the value relating to the measured impedance takes a minimum value. If the value relating to the measured impedance takes the minimum value, the control transitions to the third control.

If moisture evaporates in the second control, the value relating to the impedance increases subsequently in accordance with the rise in temperature. In the third control, the output control is executed such that the value relating to the impedance increases linearly. In this third period, the temperature of the biological tissue is kept substantially constant.

Hereinafter, the first to third controls will be described in detail.

[First Control]

The first control will be described with reference to a flowchart illustrated in FIG. 5.

In step S201, the control circuit 210 causes the high-frequency electric power source circuit 220 to supply AC electric power having a predetermined electric power value to the biological tissue that is the treatment target, which is clamped between the first grasping member 112 and second grasping member 114. By the supply of the AC electric power, an AC current flows through the biological tissue.

In step S202, the control circuit 210 acquires an impedance value relating to the biological tissue that is the treatment target. For example, the control circuit 210 acquires the current detected by the current detection circuit 231 of the output detection circuit 230, and the voltage detected by the voltage detection circuit 232 of the output detection circuit 230, and calculates the impedance value based on these values. Here, the calculated impedance value may be various kinds of values relating to the impedance, and may be, for example, an absolute value of the impedance which is a complex number, or may be a resistance value which is a real number component of the impedance. An admittance, which is a reciprocal of the impedance, may be used.

In step S203, the control circuit 210 determines whether a predetermined time has passed. Here, the predetermined time is, for example, 100 milliseconds. If the predetermined time has not passed, the process returns to step S201. Specifically, the supply of the predetermined electric power and the acquisition of the impedance value are repeated. When the predetermined time has passed, the first control ends, and a transition occurs to the second control.

The impedance value, which is acquired in the first control, is referred to as an initial impedance value. The initial impedance value may be an impedance value which is first acquired, or may be a mean value or a median of impedance values acquired in some periods in the first period during which the first control is executed.

[Second Control]

The second control will be described in detail. The second control is a control which is optimized in order to stably seal a blood vessel or the like. Here, attention is paid to a change of the impedance value at a time when the biological tissue, such as a blood vessel, is heated. If the biological tissue is heated, the temperature of an electrolyte solution in the biological tissue rises, and the impedance decreases. Paying attention to this decrease of the impedance, the following became clear.

FIG. 6 illustrates the relationship between duration of a voltage application (heating time) by the second control and a mean value of a vessel burst pressure (VBP). Here, the duration of the voltage application by the second control is a time from when the second control started until when the impedance value takes the minimum value, as described above. In addition, as described above and as illustrated in FIG. 4, the second control is a control in which the output voltage is adjusted so as to increases linearly. The VBP indicates a pressure at which a sealed part is peeled when a water pressure is applied to the blood vessel after the seal treatment through the second control and third control. Specifically, as the VBP becomes higher, this means that stronger sealing is performed. In general, it is required that a VBP of 360 mmHg or above be obtained in the blood vessel after at least 90% or more of the treatment. As illustrated in FIG. 6, the VBP tends to increase, as the time until the impedance value takes the minimum value becomes longer. In addition, even when the time until the impedance value takes the minimum value increased to one second or more, the VBP did not increase so much.

Taking into account the result shown in FIG. 6 and the fact that a shorter treatment time is desired, it is considered that the time until the impedance value takes the minimum value should preferably be about one second. It is understood that the time may be in a range of between about 0.5 seconds and 1.5 seconds, in which the VBP is sufficiently higher than 360 mmHg. In consideration of these results, in the present embodiment, the output voltage in the second control is adjusted such that the time until the impedance value takes the minimum value becomes about one second.

In the present embodiment, the control circuit 210 controls the output voltage V(t) which is applied to the biological tissue in the second control, as indicated by the following equation (1):

$$V(t)=(V(Z)/GV) \times t, \tag{1}$$

where t is a time from the start of treatment, that is, a time from the start of the first control. The time t may be a time from the start of the second control. V(Z) is a constant, for example, a maximum value of the output voltage. GV is a gradient value. Thus, (V(Z)/GV) indicates an increase value of the output voltage per unit time, that is, an inclination (increase rate).

GV is determined based on the initial impedance value acquired in the first control. For example, based on an initial resistance value R0, GV is determined by the following equation (2):

$$GV = a \cdot R0 + b, \quad (2)$$

where a and b are fixed values. The values a and b are empirically adjusted such that the impedance value takes the minimum value in about one second, when the output voltage V(t) applied to the biological tissue.

The above equation (2) is not limited to an equation of a linear function, and may be another equation such as a function of a higher degree. However, the linear function is preferable to a higher-degree function, so that the influence, which the initial resistance value R0 exerts on the above equation (1), may not become excessively large. In addition, the above equation (1) is also a linear function relating to time. Because of the linear function, a proper temperature rise with high stability can be obtained. Since the output voltage is the linear function relating time, the electric power, which is input to the biological tissue, increases in a manner of a quadratic function with respect to time. An offset may be added to the output voltage V(t). Specifically, the above equation (1) may be modified as follows:

$$V(t) = (V(Z)/GV) \times t + c, \quad (3)$$

where c is a fixed value.

According to the above equations (1) and (2), for example, in a thin blood vessel, the initial resistance value R0 is relatively high. Thus, (V(Z)/GV), which indicates a gradient, is relatively small. Specifically, in a thin blood vessel, the output voltage increases relatively slowly, and accordingly the input electric power increases relatively slowly. On the other hand, for example, in a thick blood vessel, the initial resistance value R0 is relatively low. Thus, (V(Z)/GV), which indicates the gradient, is relatively large. Specifically, in a thick blood vessel, the output voltage increases relatively quickly, and accordingly the input electric power increases relatively quickly.

The gradient (V(Z)/GV) may be calculated at each time and used, based on the relationships of the above equations (1) and (2) and the initial resistance value R0, or may be determined based on the table prestored in the storage medium 250, which represents the relationship between the initial resistance value R0 and gradient (V(Z)/GV), and based on the initial resistance value.

Figure 7:
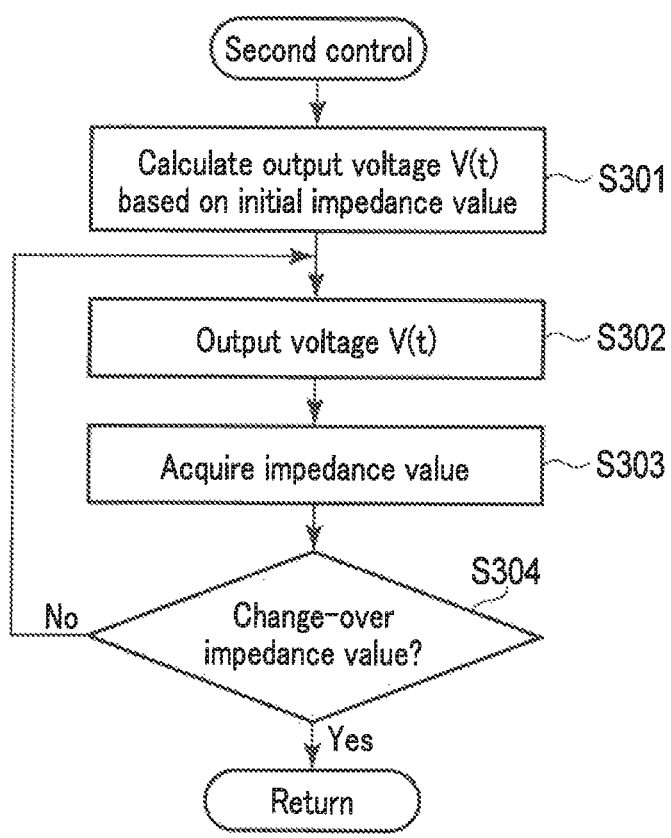
FIG. 7 is a flowchart illustrating an example of the second control of the high-frequency treatment system according to the embodiment.

The operation of the electric power source device 200 in the second control will be described with reference to a flowchart of FIG. 7.

In step S301, the control circuit 210 calculates the relationship between time and output voltage V(t), based on the initial impedance value. The output voltage V(t) is determined, for example, by using the above equations (1) and (2).

In step S302, the control circuit 210 causes the high-frequency electric power source circuit 220 to output the voltage V(t) which corresponds to time. In step S303, the control circuit 210 acquires the impedance value of the biological tissue.

In step S304, the control circuit 210 determines whether the impedance value acquired in step S303 is a change-over impedance value or not. Here, the change-over impedance value is an impedance value which is a condition for terminating the second control. The change-over impedance value can be, for example, a value at a time when the variation of the impedance value is measured and the impedance value becomes the minimum value. In order to easily detect the minimum value, a value, which has increased by a predetermined value after the impedance value took the minimum value, may be set as the change-over impedance value. Specifically, in step S304, when the impedance value decreased and took the minimum value and then the impedance value has increased by the predetermined value, it may be determined that the impedance value has become the change-over impedance value. In step S304, when it is determined that the impedance value is not the change-over impedance value, the process returns to step S302. On the other hand, when it is determined that the impedance value is the change-over impedance value, the second control is terminated, and a transition occurs to the third control.

By the above-described controls, the output voltage and the impedance value become as illustrated in FIG. 4. Specifically, in the second period in which the second control is executed, the output voltage increases linearly. At this time, the output electric power increases in a manner of a quadratic function. The impedance value acquired in the second period decreases slowly with time, in the example illustrated in FIG. 4, when the impedance value has slightly increased after taking the minimum value, the second control is terminated, in the meantime, although the example in which the output voltage is controlled is illustrated here, the output current or output electric power may be controlled so as to increase linearly in the same manner.

The time until the impedance value takes the minimum value is set to be about one second and is relatively slow. It is thus possible to make uniform the temperature of the biological tissue, while shortening the time of the treatment. In addition, by setting the time until the impedance value takes the minimum value to be constant at about one second, regardless of the size, etc. of the treatment target, it is possible to suppress a variance in results of treatments. In the meantime, when the same energy is input, the impedance value takes the minimum value in a shorter time, as the thickness of the blood vessel becomes smaller. By setting the time until the impedance value takes the minimum value to be about one second, a high sealing strength can be obtained stably, as illustrated in FIG. 6.

[Third Control]

The third control will be described in detail. In the third control, the output is controlled such that the measured impedance value increases with a constant rate. In the present embodiment, a stop impedance value, which is an impedance value at a time when the output is stopped, is first determined. Next, target impedance which increases at a constant speed from the impedance value at the start time of the third control up to the stop impedance value is set. Specifically, the target impedance value is set as a target value of the impedance value at each time. The control of the output is executed such that the output value is determined at predetermined time intervals, based on a difference between the target impedance value and a measured impedance value acquired by using the output detection circuit 230. In this manner, the third control is executed until the measured impedance value reaches the stop impedance value along target impedance values.

<Setting of the Stop Impedance Value in the Third Control>

A determination method of the stop impedance value at the time of stopping the output will be described. Here, a description is given of the case of using a resistance value as the impedance value. The same applies to cases using other impedance values, aside from the resistance value. A stop resistance value Rstop, which is a resistance value at the time of stopping the output, is calculated by, for example, the following equation (4):

$$R{stop}=R{in}+R{add}. \quad (4)$$

Rin is a resistance value relating to the biological tissue, which is acquired at the start time of the third control. Specifically, Rin is the resistance value corresponding to the above-described change-over impedance value. The Rin may be the minimum impedance measured in the second control. In addition, the initial impedance value acquired in the first control may be used for Rin.

Radd is an additional resistance value which is determined based on the initial state of the biological tissue. Some examples of the determination method of the additional resistance value Radd will be illustrated.

First Example

Figures 8, 9, 10:
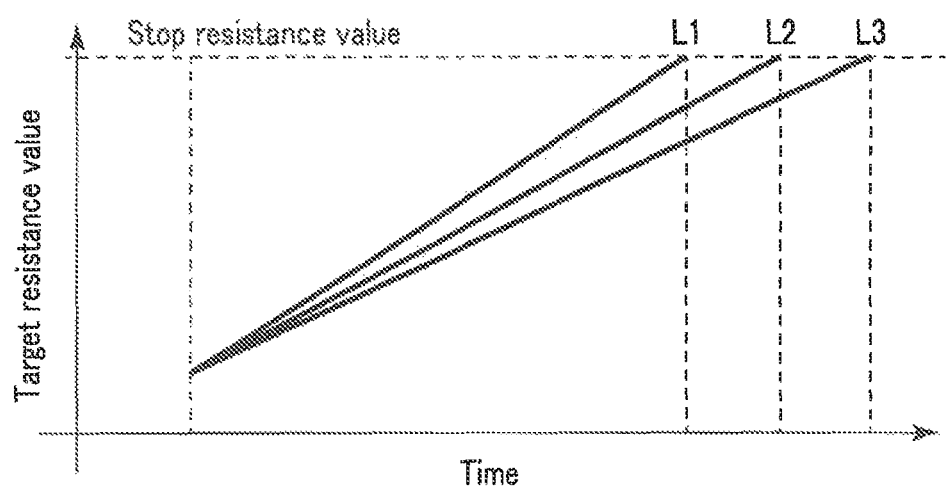
FIG. 8 shows an example of a table including a relationship between an initial resistance value and an additional resistance value, which are used in the high-frequency treatment system according to the embodiment.
FIG. 9 shows an example of a table including a relationship between an initial resistance value, duration and an additional resistance value, which are used in the high-frequency treatment system according to the embodiment.
FIG. 10 shows an example of a graph of a target resistance value versus time in the high-frequency treatment system according to the embodiment.

The additional resistance value Radd is calculated as a function of the initial resistance value R0. The initial resistance value R0 is the resistance value detected in the first control. The storage medium 250 stores a table, for example, as illustrated in FIG. 8, the table representing the relationship between the additional resistance value Radd and initial resistance value R0. Based on this table and the initial resistance value R0 measured in the first control, the additional resistance value Radd is determined. In FIG. 8, a, b, c and d represent resistance values, and have a relationship of a<b<c<d. Specifically, as the initial resistance value R0 becomes higher, the additional resistance value Radd becomes lower. In other words, when the treatment target is a blood vessel, a thinner blood vessel has a higher initial resistance R0, and thus the additional resistance value Radd becomes lower. In addition, the additional resistance value Radd may be calculated based on a function representing the same relationship as in FIG. 8.

Second Example

The additional resistance value Radd is calculated as a function of the initial resistance value R0 and duration Dt of the second control. The duration Dt is acquired when the second control is finished. For example, when the initial resistance value R0 is a predetermined threshold value or more, and when the duration Dt is a predetermined threshold value or less, a first additional resistance value Radd1 is selected as the additional resistance value Radd. When the initial resistance value R0 is lower than the predetermined threshold value, or when the duration Dt is longer than the predetermined threshold value, a second additional resistance value Radd2 is selected as the additional resistance value Radd. Here, the first additional resistance value Radd1 is lower than the second additional resistance value Radd2.

In addition, the storage medium 250 stores a table, for example, as illustrated in FIG. 9, the table representing the relationship between the additional resistance value Radd, duration Dt and initial resistance value R0. Based on this table, the initial resistance value R0 measured in the first control and the duration Dt of the second control, the additional resistance value Radd may be determined. In FIG. 9, a, b, c and d represent resistance values, and have a relationship of a<b<c<d. Specifically, as the initial resistance value R0 becomes higher, the additional resistance value Radd becomes lower; and as the duration Dt becomes longer, the additional resistance value Radd becomes higher.

In addition, the additional resistance value Radd may be calculated based on a function representing the same relationship as in FIG. 9.

Based on the initial resistance value R0 and the duration Dt of the second control, the additional resistance value Radd is determined. Thereby, a more appropriate additional resistance value Radd can be determined than in the case in which the additional resistance value Radd is determined based on only the initial resistance value R0.

Third Example

The additional resistance value Radd may be selected in accordance with an output level which the user sets. For example, as the output level becomes higher, the additional resistance value Radd becomes higher; and as the output level becomes lower, the additional resistance value Radd becomes lower. It is preferable that, like the case of the first example or the second example, the output level is used in combination with the initial resistance value R0 or the duration Dt of the second control. A more appropriate value can be set, by the additional resistance value. Radd being determined by using the output level in combination with the initial resistance value R0 or the duration Dt of the second control.

In each of the above first to third examples, for instance, as the blood vessel becomes thinner, the additional resistance value Radd becomes lower; and as the blood vessel becomes thicker, the additional resistance value Radd becomes higher. The stop resistance value Rstop is higher than the initial resistance value R0.

Like the above, when a value relating to the impedance, other than the resistance value, is used, Rin corresponds to the change-over impedance value, the additional resistance value Radd corresponds to the additional impedance value, and the initial resistance value R0 corresponds to the initial impedance value.

As described above, use is made of the initial impedance value which varies in accordance with the treatment target, for instance, the thickness of the blood vessel. Thereby, the stop impedance value corresponding to the treatment target is appropriately set. Since the output control is executed by using the thus determined stop impedance value, a proper treatment can be performed.

<Setting of the Target Impedance Value in the Third Control>

A setting method of the target impedance value will be described. Here, a description is given of the case in which, like the above-described stop resistance value, the resistance value is used as the impedance value. Specifically, the case in which a target resistance value is used as the target impedance value will be described. The same applies to the cases of using other values relating to the impedance, aside from the resistance value.

First Example

In a first example, a time in which high-frequency electric power is output by the third control is predetermined. A target resistance value at each time can be set such that, in this predetermined time, the resistance value linearly increases up to the stop resistance value Rstop which is calculated from the change-over resistance value Rin.

Second Example

In a second example, a time in which high-frequency electric power is output by the third control is determined in accordance with the output level that is set by the user. A target resistance value can be set such that, in the time determined in accordance with the output level, the resistance value linearly increases up to the calculated stop resistance value Rstop. Specifically, as illustrated in FIG. 10, an inclination at a time when the target resistance value is indicated relative to time varies in accordance with the output level. In other words, the speed of increase of the target resistance value varies in accordance with the output level. In FIG. 10, L1, L2 and L3 indicate output levels, and have a relationship of L1<L2<L3.

Third Example

In a third example, a time in which high-frequency electric power is output by the third control is determined in accordance with the resistance value (initial resistance value) acquired in the first control. In addition, the time in which high-frequency electric power is output by the third control may be determined in accordance with the resistance value acquired in the second control. A target resistance value can be set such that, in the determined time, the resistance value linearly increases up to the calculated stop resistance value Rstop. Specifically, an inclination at a time when the target resistance value is indicated relative to time varies in accordance with the resistance value acquired in the first control or second control. In other words, the speed of increase of the target resistance value varies in accordance with the resistance value acquired in the first control or second control. For example, when the resistance value acquired in the first control or second control is low, the output time in the third control becomes shorter and the inclination becomes larger. On the other hand, when the resistance value acquired in the first control or second control is high, the output time in the third control becomes longer and the inclination becomes smaller.

<Determination Method of Output Electric Power in the Third Control>

A determination method of an output will be described. Like the above-described case, the case in which a resistance value is used as the impedance value is described. The same applies to the cases of using other values relating to the impedance, aside from the resistance value.

A description will be given with reference to FIG. 11. An upper part FIG. 11 schematically illustrates a target resistance value and a measured resistance value relative to time. Here, the target resistance value is indicated by a broken line, and the measured resistance value is indicated by a solid line. A lower part of FIG. 11 schematically illustrates output electric power relative to time. In the present embodiment, the output electric power is set in each step time of several-ten milliseconds. The setting of the output electric power is executed by comparing the target resistance value and the measured resistance value. Specifically, the target resistance value and the measured resistance value are compared at predetermined time intervals. When the measured resistance value is higher than the target resistance value, the output electric power is decreased. On the other hand, when the measured resistance value is lower than the target resistance value, the output electric power is increased. In addition, when the difference between the measured resistance value and the target resistance value is less than a predetermined threshold value, the output electric power is maintained. The output electric power at the start time of the third control may be the output electric power at the end time of the second control. The output electric power at the start time of the third control may be a predetermined value, or may be determined by a predetermined method.

If the set value of the output electric power is frequently changed, there is concern that the output oscillates. On the other hand, if the setting of the output electric power is executed only occasionally, the precision in control would lower, or the treatment could not be completed within a target time. Thus, it is preferable that the interval of re-setting of output electric power, that is, the step time, is appropriately adjusted. Examples of the determination method of the output electric power will be described.

First Example

In a first example, a change amount of the output electric power is a predetermined ratio relative to the output electric power at that time point. For example, this predetermined ratio is set as a first ratio. In this case, when the initial output electric power a first electric power, and the measured resistance value is higher than the target resistance value, the next output electric power is set at a second electric power which is lowered from the first electric power by the first ratio. When the output is a second electric power, and the measured resistance value is lower than the target resistance value, the next output electric power is set at a third electric power which is raised from the second electric power by the first ratio. Subsequently, the output electric power is controlled in the same manner. For example, if the first ratio is set at 10%, the output electric power is controlled as follows. When the output electric power is 20 W at that time point and the measured resistance value is higher than the target resistance value, the next output electric power is adjusted at 18 W. When the output electric power is 18 W and the measured resistance value is lower than the target resistance value, the next output electric power is adjusted at 19.8 W. By setting the change amount of the output electric power to be the predetermined ratio relative to the output electric power at that time point, the change amount is adjusted to a proper value at each of a time when the output electric power is large and a time when the output electric power is small. The numerical values illustrated here are merely examples, and any numerical value can be used for the proper setting.

In the meantime, when the ratio at the time of lowering the output electric power is set as a first ratio and the ratio at the time of raising the output electric power is set as a second ratio, the first ratio and the second ratio may be equal or different. It is preferable that the first ratio is greater than the second ratio. For example, when the measured resistance value is higher than the target resistance value, the output is lowered by 10%. When the measured resistance value is lower than the target resistance value, the output is raised by 5%. In addition, when the difference between the measured resistance value and the target resistance value is within a predetermined range, the output electric power may not be changed.

Second Example

In a second example, a change amount of the output electric power is a predetermined value. In a case in which this predetermined ratio is set as a first value, when the measured resistance value is higher than the target resistance value, the next output electric power is adjusted at a value which is lowered from the present output electric power by a first value. When the measured resistance value is lower than the target resistance value, the next output electric power is adjusted at a value which is higher than the present output electric power by the first value. For example, when the change amount is set to be 2 W, the output electric power is controlled as follows. When the output electric power is 20 W at that time point and the measured resistance value is higher than the target resistance value, the next output electric power is adjusted at 18 W. When the output electric power is 18 W and the measured resistance value is lower than the target resistance value, the next output electric power is adjusted at 20 W. By setting the change amount of the output electric power at a constant value, the hardware configuration becomes simpler, and the control of the output electric power becomes easier. The numerical values illustrated here are merely examples, and any numerical value can be used for the proper setting.

In the meantime, the change amount at the time of raising the output and the change amount at the time of lowering the output may be equal or different. It is preferable that the change amount at the time of lowering the output is greater than the change amount at the time of raising the output. In addition, when the difference between the measured resistance value and the target resistance value is within a predetermined range, the output electric power may not be changed.

Third Example

In a third example, a change amount of the output electric power is determined based on the initial resistance value R0 acquired in the first control, and the length of the second period in which the second control is executed, that is, the period from when the second control started until when the impedance values takes the minimum value. Thus, the storage medium 250 prestores, for example, a relationship between the initial resistance value R0, the length of the second period, and the change amount of the output electric power. The control circuit 210 determines the output electric power by referring to this relationship.

Fourth Example

In a fourth example, a change amount of the output electric power is a predetermined value which is determined in accordance with an output level that is set by the user. The storage medium 250 prestores a relationship between the output level and the change amount of the output electric power. The control circuit 210 determines the output electric power by referring to this relationship.

Fifth Example

In a fifth example, the output electric power is determined by the relationship between the measured resistance value and the target resistance value. For example, the output electric power is set as follows. When the measured resistance value higher than the target resistance value, the output electric power is set at a first electric power value. When the measured resistance value is equal to the target resistance value, the output electric power is set at a second electric power value. When the measured resistance value is lower than the target resistance value, the output electric power is set at a third electric power value. Here, the electric power values become greater in the order of the first electric power value, second electric power value and third electric power value. For example, the first electric power value is 5 W, second electric power value is 8 W, and third electric power value is 10 W. The numerical values illustrated here are merely examples, and any numerical value can be used for the proper setting.

The third control, which is controlled in the above manner, will be described with reference to a flowchart of FIG. 12.

In step S401, the control circuit 210 calculates the additional impedance value, based on the initial impedance value. In step S402, the control circuit 210 sets the stop impedance value, based on the sum of the change-over impedance value and the additional impedance value. For example, any of the methods of the above-described first to third examples may be used for the setting method of the stop impedance value.

In step S403, the control circuit 210 sets the target impedance value by using the stop impedance value. Any of the methods of the above-described first to third examples may be used for the setting method of the target impedance value. In step S404, the control circuit 210 causes the high-frequency electric power source circuit 220 to output, as an initial electric power, the electric power having a predetermined electric power value. The initial electric power is, for example, the electric power at the time of the end of the second control.

In step S405, the control circuit 210 acquires the impedance value by using the value detected by the output detection circuit 230. In step S406, the control circuit 210 determines whether the measured impedance value is the stop impedance value or more. When the measured impedance value is not the stop impedance value or more, the process advances to step S407.

In step S407, the control circuit 210 compares the measured impedance value (Zm) and the target impedance value (Zt). When the difference between the measured impedance value (Zm) and the target impedance value (Zt) is within a predetermined threshold value (Zm≈Zt), the process advances to step S408. In step S408, the control circuit 210 maintains the set value (set electric power) of the output electric power. Thereafter, the process advances to step S411. In step S407, when it is determined that the measured impedance value (Zm) is greater than the target impedance value (Zt) (Zm>Zt), the process advances to step S409. In step S409, the control circuit 210 sets the set electric power to a low electric power. Then, the process advances to step S411. In step S407, when it is determined that the measured impedance value (Zm) is less than the target impedance value (Zt) (Zm<Zt), the process advances to step S410. In step S410, the control circuit 210 sets the set electric power to a high electric power. Then, the process advances to step S411. For example, any of the methods of the above-described first to fifth examples may be used for the method of setting the electric power in each of step S408 to step S410.

In step S411, the control circuit 210 causes the high-frequency electric power source circuit 220 to output the electric power of the electric power value which is set in any one of steps S408 to step S410. Thereafter, the process returns to step S405.

In step S406, when it is determined that the measured impedance is the stop impedance value or more, the process advances to step S412. In step S412, the control circuit 210 causes the high-frequency electric power source circuit 220 to stop the output. Then, the third control is finished. By the above, the supply of the high-frequency electric power to the high-frequency treatment instrument 100 by the electric power source device 200 is terminated.

According to the above-described control, the output and the acquired impedance value are as illustrated in FIG. 4. Specifically, in the third control, the impedance value increases linearly. The output electric power (output voltage or output current) is adjusted such that the impedance value increases linearly.

According to the above-described third control, the impedance value increases linearly, and thus the temperature of the biological tissue is kept substantially constant. In this manner, the treatment of the biological tissue progresses at substantially constant temperatures. Thus, for example, the stable sealing of the blood vessel can be obtained.

In addition, since the stop impedance value, which corresponds to the characteristics of the biological tissue, is determined, the condition for finishing the treatment, which corresponds to the characteristics of the biological tissue, is determined. Specifically, the treatment is finished at a time point when sufficient treatment is conducted, regardless of differences in characteristics of biological tissues which are treatment targets.

As described above, according to the present embodiment, in the high-frequency treatment system 10, the output, which is optimized in accordance with the treatment target, can be executed.

The above description of the embodiment is given by taking, mainly, the sealing of the blood vessel as an example. However, the above-described technique is applicable to treatments of other biological tissues. In addition, the above-described operation may be prepared as a mode for sealing a blood vessel, and this mode may be prepared as well as other modes in the high-frequency treatment system 10. The high-frequency treatment system 10 may be configured such that the user can select a mode corresponding to a treatment, from among these modes.

The high-frequency treatment system 10 according to the present embodiment may be configured not only to output the high-frequency electric power, but also to have a function as an ultrasonic treatment instrument, which treats a biological tissue by ultrasonic vibration, for example, by the first grasping member 112 vibrating at an ultrasonic frequency. A treatment instrument, which also uses ultrasonic energy, can function in the same manner as in the above-described embodiment with respect to the output of the high-frequency electric power.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An operation method of an electric power source device for operating a high-frequency treatment instrument configured to perform a high-frequency treatment on a biological tissue, the operation method comprising:
   causing, by a control circuit, a high-frequency electric power source circuit to output electric power;
   specifying, by the control circuit, an initial state of the biological tissue in a first period from a start of the output, wherein the initial state includes an initial impedance value which is a first value relating to an impedance of the biological tissue and is acquired based on the output;
   acquiring, by the control circuit, a second value relating to an impedance of the biological tissue, after specifying the initial state of the biological tissue;
   acquiring, by the control circuit after the second value relating to the impedance reached a change-over impedance value, a length of a second period, wherein
      the change-over impedance value is a value relating to the impedance indicative of a predetermined state, and
      the second period starts after specifying the initial state ends when the second value relating to the impedance reaches the change-over impedance value;
   determining, by the control circuit, an additional impedance value, based on a prestored table in which the initial impedance value, the length of the second period and the additional impedance value are associated;
   setting, by the control circuit, a stop impedance value which is the sum of the additional impedance value and the change-over impedance value; and
   causing, by the control circuit, the high-frequency electric power source circuit to stop the output, if the value relating to the impedance reaches the stop impedance value after the value relating to the impedance reached the change-over impedance value.

2. The operation method of claim 1, wherein the change-over impedance value is a minimum value of the second value relating to the impedance which is measured after specifying the initial state.

3. The operation method of claim 1, wherein the change-over impedance value is a value which is greater, by a predetermined value, than a minimum value of the second value relating to the impedance which is measured after specifying the initial state.

4. The operation method of claim 1, further comprising, controlling, by the control circuit, an output voltage of the high-frequency electric power source circuit in the second period based on the initial impedance value.

5. The operation method of claim 4, wherein the control circuit controls the output voltage to linearly increase in the second period.

6. The operation method of claim 1, further comprising
   setting, by the control circuit, a target impedance value so that the second value relating to the impedance increases at a constant speed in a third period from when the second value relating to the impedance has reached the change-over impedance value to when the second value relating to the impedance has reached the stop impedance value, and
   controlling, by the control circuit, the output of the high-frequency electric power source circuit based on a difference between the target impedance value and the second value relating to the impedance.

7. The operation method of claim 1, wherein
a length of the first period is shorter than the length of the second period, and the length of the second period is shorter than a length of a third period from when the second value relating to the impedance has reached the change-over impedance value to when the second value relating to the impedance has reached the stop impedance value.

8. An electric power source device for operating a high-frequency treatment instrument configured to perform a high-frequency treatment on a biological tissue, the device comprising:
   a high-frequency electric power source circuit configured to output electric power;

an output detection circuit configured to detect the output; and a control circuit configured to acquire information relating to the output from the output detection circuit, and configured to control an operation of the high-frequency electric power source circuit, the control circuit being configured to execute:
- causing the high-frequency electric power source circuit to output the electric power;
- specifying an initial state of the biological tissue in a first period from a start of the output, wherein the initial state includes an initial impedance value which is a first value relating to an impedance of the biological tissue and is acquired based on the output;
- acquiring a second value relating to an impedance of the biological tissue, after specifying the initial state of the biological tissue;
- acquiring, by the control circuit after the second value relating to the impedance reached a change-over impedance value, a length of a second period, wherein
  - the change-over impedance value is a value relating to the impedance indicative of a predetermined state, and
  - the second period starts after specifying the initial state ends when the second value relating to the impedance reaches the change-over impedance value;
- determining an additional impedance value, based on a prestored table in which the initial impedance value, the length of the second period and the additional impedance value are associated;
- setting a stop impedance value which is the sum of the additional impedance value and the change-over impedance value; and
- causing the high-frequency electric power source circuit to stop the output, if the value relating to the impedance reaches the stop impedance value after the value relating to the impedance reached the change-over impedance value.

9. A high-frequency treatment system comprising:
the electric power source device of claim 8; and
the high-frequency treatment instrument.

10. The electric power source device of claim 8, wherein the control circuit is further configured to control an output voltage of the high-frequency electric power source circuit in the second period based on the initial impedance value.

11. The electric power source device of claim 10, wherein the control circuit is configured to control the output voltage to linearly increase in the second period.

12. The electric power source device of claim 8, wherein the control circuit is further configured to
- set a target impedance value so that the second value relating to the impedance increases at a constant speed in a third period from when the second value relating to the impedance has reached the change-over impedance value to when the second value relating to the impedance has reached the stop impedance value, and
- control the output of the high-frequency electric power source circuit based on a difference between the target impedance value and the second value relating to the impedance.

13. The electric power source device of claim 8, wherein a length of the first period is shorter than the length of the second period, and the length of the second period is shorter than a length of a third period from when the second value relating to the impedance has reached the change-over impedance value to when the second value relating to the impedance has reached the stop impedance value.

* * * * *